United States Patent
Bouphavichith et al.

(10) Patent No.: US 8,187,253 B2
(45) Date of Patent: *May 29, 2012

(54) LOW PROFILE ADAPTOR FOR USE WITH A MEDICAL CATHETER

(75) Inventors: Laddvanh Bouphavichith, Worcester, MA (US); Michael S. H. Chu, Brookline, MA (US); Laurence D. Brenner, Boylston, MA (US); William L. Churchill, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/626,246

(22) Filed: Nov. 25, 2009

(65) Prior Publication Data

US 2010/0076383 A1    Mar. 25, 2010

Related U.S. Application Data

(63) Continuation of application No. 10/911,098, filed on Aug. 4, 2004, now Pat. No. 7,641,648, which is a continuation of application No. 10/078,223, filed on Feb. 19, 2002, now Pat. No. 6,802,836.

(51) Int. Cl.
*A61M 25/16* (2006.01)

(52) U.S. Cl. ......... 604/535; 604/246; 604/250; 604/537

(58) Field of Classification Search .......... 604/246–247, 604/250, 533–537
See application file for complete search history.

(56) References Cited

U.S. PATENT DOCUMENTS 48,709 A * 7/1865 Emory .......................... 285/251

(Continued)

FOREIGN PATENT DOCUMENTS

DE    3314640 A1    11/1983

(Continued)

OTHER PUBLICATIONS

Printout of www.barblock.com on Mar. 27, 2003.

(Continued)

*Primary Examiner* — Theodore Stigell
(74) *Attorney, Agent, or Firm* — Kenyon & Kenyon LLP

(57) ABSTRACT

A low profile adaptor for use with a medical catheter. In one embodiment, the adaptor comprises a lower connector portion, an upper connector portion and a valve. The lower connector portion comprises a tubular portion and an annular portion, the annular portion radially surrounding the tubular portion along an intermediate length thereof. A helical thread is formed on the inside surface of the tubular portion. A circular lip projects upwardly a short distance from the top surface of the annular portion. The upper connector portion comprises a tubular section adapted for insertion into the tubular portion of the lower connector portion. An external helical thread is formed on the tubular section of the upper connector portion for mating engagement with the thread on the interior of the tubular portion of the lower connector portion. The upper connector portion also includes an annular base. The top of the base is shaped to include a cavity for receiving the valve, the cavity being in fluid communication with the tubular section. A double-walled circular lip is formed on the bottom of the base, the double-walled lip being sized and shaped to define a groove adapted to matingly receive the lip on the upper connector portion. In use, the lower connector portion is inserted into the end of a catheter, and the tubular section of the upper connector portion is screwed into the tubular portion of the lower connector, with the catheter being ensnared between the lips of the upper and lower connector portions.

16 Claims, 11 Drawing Sheets

U.S. PATENT DOCUMENTS

| | | | |
|---|---|---|---|
| 362,297 A | 5/1887 | Albee et al. | |
| 1,217,203 A * | 2/1917 | Muehlberg | 285/247 |
| 2,782,058 A | 2/1957 | Clingman et al. | |
| 3,484,121 A | 12/1969 | Quinton | |
| 3,638,649 A | 2/1972 | Ersek | |
| 3,876,234 A | 4/1975 | Harms | |
| 3,926,187 A | 12/1975 | Iglesias | |
| 4,187,848 A | 2/1980 | Taylor | |
| 4,306,545 A | 12/1981 | Ivan et al. | |
| 4,390,017 A | 6/1983 | Harrison et al. | |
| 4,393,873 A | 7/1983 | Nawash et al. | |
| 4,417,890 A | 11/1983 | Dennehey et al. | |
| 4,424,833 A | 1/1984 | Spector et al. | |
| 4,473,369 A | 9/1984 | Lueders et al. | |
| 4,511,163 A | 4/1985 | Harris et al. | |
| 4,557,261 A | 12/1985 | Rugheimer | |
| 4,586,691 A * | 5/1986 | Kozlow | 251/7 |
| 4,588,402 A | 5/1986 | Igari et al. | |
| 4,642,091 A | 2/1987 | Richmond | |
| 4,774,944 A | 10/1988 | Mischinski | |
| 4,826,477 A | 5/1989 | Adams | |
| 4,834,712 A | 5/1989 | Quinn et al. | |
| 4,861,334 A | 8/1989 | Nawaz | |
| 4,863,438 A | 9/1989 | Gauderer et al. | |
| 4,895,570 A | 1/1990 | Larkin | |
| 4,900,306 A | 2/1990 | Quinn et al. | |
| 4,944,732 A | 7/1990 | Russo | |
| 4,946,200 A | 8/1990 | Blenkush et al. | |
| 4,951,976 A | 8/1990 | Boelkins | |
| 5,007,900 A | 4/1991 | Picha et al. | |
| 5,024,655 A | 6/1991 | Freeman | |
| 5,026,352 A | 6/1991 | Anderson | |
| 5,071,405 A | 12/1991 | Piontek et al. | |
| 5,100,394 A | 3/1992 | Dudar et al. | |
| 5,112,310 A | 5/1992 | Grobe | |
| 5,158,569 A | 10/1992 | Strickland et al. | |
| 5,167,627 A | 12/1992 | Clegg et al. | |
| 5,176,415 A * | 1/1993 | Choksi | 285/331 |
| 5,178,423 A | 1/1993 | Combeau | |
| 5,215,538 A | 6/1993 | Larkin | |
| 5,222,772 A | 6/1993 | McGraw | |
| 5,259,399 A | 11/1993 | Brown | |
| 5,267,983 A | 12/1993 | Oilschlager et al. | |
| 5,290,250 A | 3/1994 | Bommarito | |
| 5,323,811 A | 6/1994 | Hohmann et al. | |
| 5,358,488 A | 10/1994 | Surlyapa et al. | |
| 5,391,159 A | 2/1995 | Hirsch et al. | |
| 5,405,339 A | 4/1995 | Kohnen et al. | |
| 5,488,949 A | 2/1996 | Kreifels et al. | |
| 5,505,714 A | 4/1996 | Dassa et al. | |
| 5,549,657 A | 8/1996 | Stern et al. | |
| 5,720,734 A | 2/1998 | Copenhaver et al. | |
| 5,782,508 A | 7/1998 | Bartholomew | |
| 5,830,195 A | 11/1998 | Peters et al. | |
| 5,836,924 A | 11/1998 | Kelliher et al. | |
| 5,863,366 A | 1/1999 | Snow | |
| 6,050,987 A | 4/2000 | Rosenbaum | |
| 6,095,997 A | 8/2000 | French et al. | |
| 6,802,836 B2 * | 10/2004 | Bouphavichith et al. | 604/534 |
| 6,971,390 B1 | 12/2005 | Vasek et al. | |
| 7,641,648 B2 * | 1/2010 | Bouphavichith et al. | 604/533 |

FOREIGN PATENT DOCUMENTS

| | | |
|---|---|---|
| EP | 0976418 A1 | 2/2000 |
| GB | 2055166 A | 2/1981 |
| JP | 49148423 U | 12/1974 |
| JP | 62281962 A | 12/1987 |
| JP | 3280971 A | 12/1991 |
| JP | 3318463 B2 | 10/1996 |
| JP | 9508542 T | 9/1997 |
| JP | 9508840 T | 9/1997 |
| JP | 11141791 A | 5/1999 |
| JP | 2000506051 T | 5/2000 |
| WO | 95/20936 A1 | 8/1995 |
| WO | 95/22369 A1 | 8/1995 |
| WO | 9520936 A1 | 8/1995 |
| WO | 9732623 A1 | 9/1997 |

OTHER PUBLICATIONS

European Patent Office, International Search Report from PCT/US2004/015541, the corresponding PCT application to the present application, dated Nov. 19, 2004.

Australian Patent Office, Examiner's First Report on related patent application No. 2003205762, dated Jul. 27, 2007.

Japan Patent Office, Office Action in related Japanese patent application No. 2006-533180, dated Nov. 24, 2009.

Japan Patent Office, Office Action in related Japanese patent application No. 2003-569111, dated Jan. 5, 2010.

European Patent Office, partial International Search Report in corresponding International Application No. PCT/EP03/01443, mailed Nov. 10, 2003.

Japan Patent Office, Office Action in Japanese patent application No. 2003-569111, dated Mar. 17, 2009.

Japan Patent Office, Office Action in Japanese patent application No. 2006-533180, dated Aug. 31, 2010.

* cited by examiner

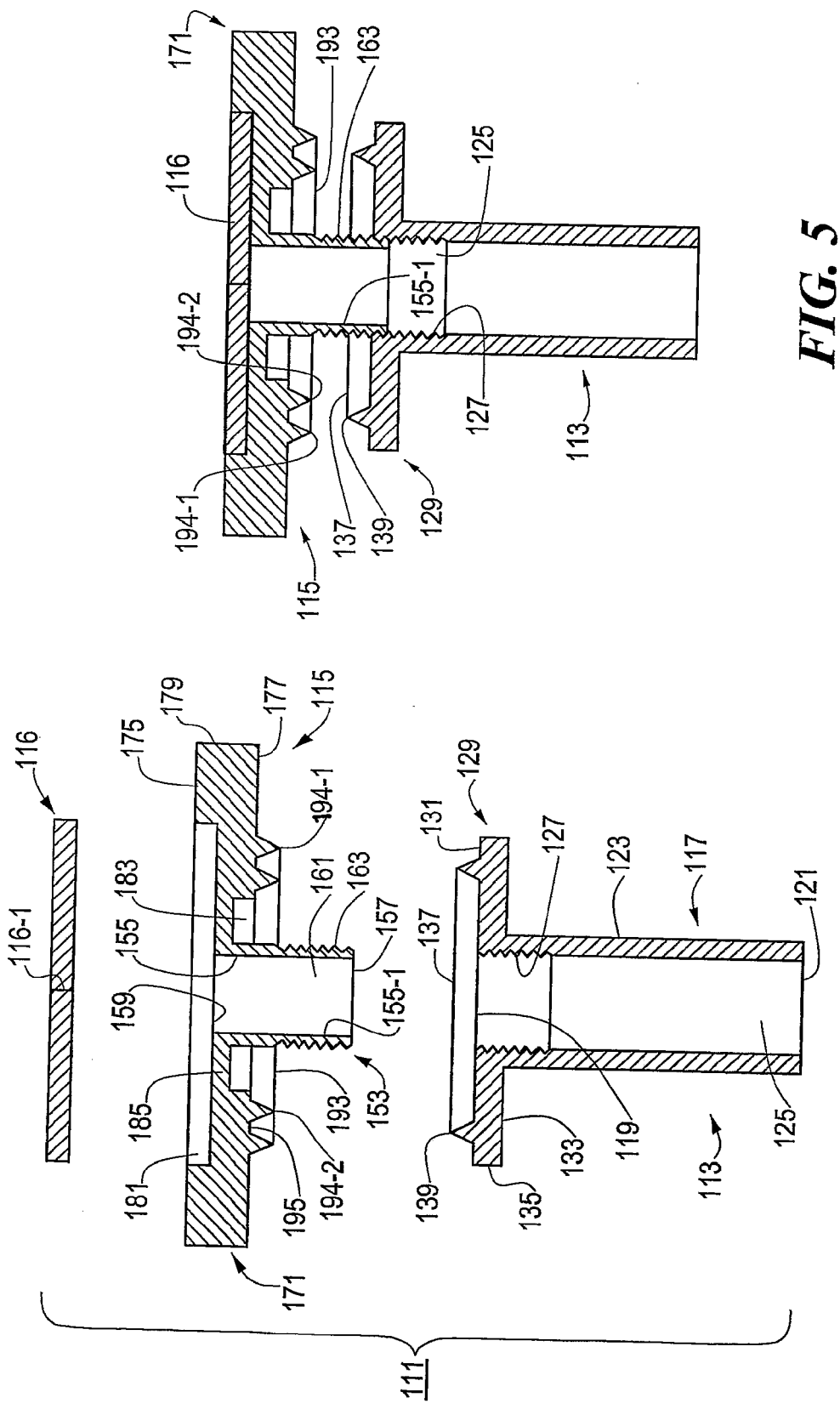

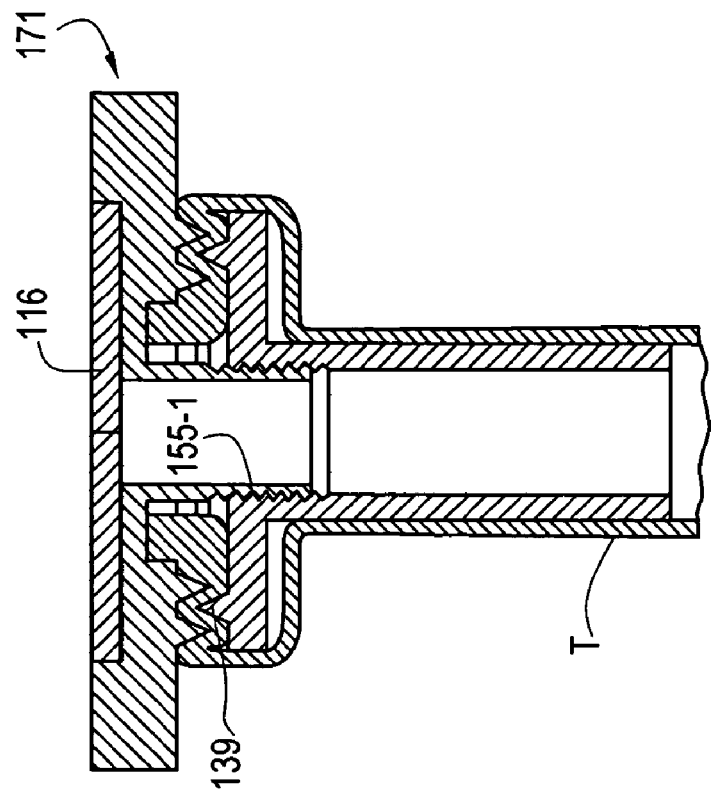
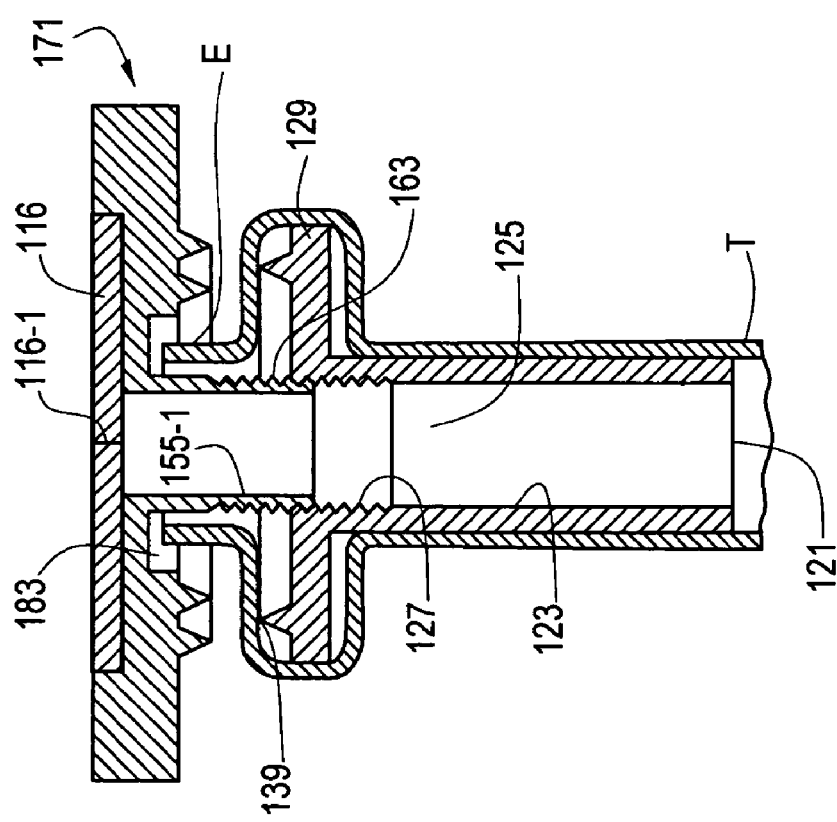

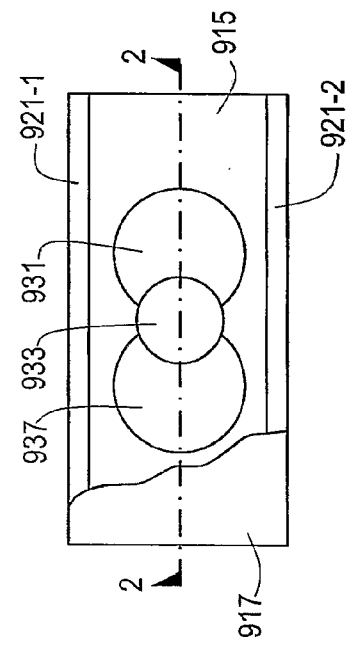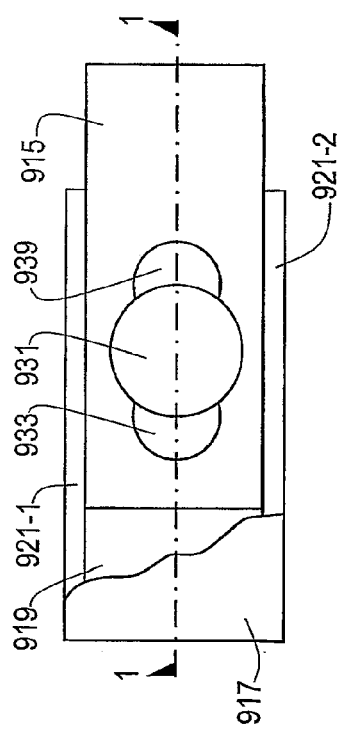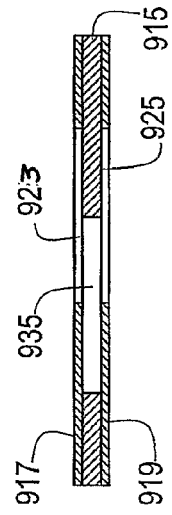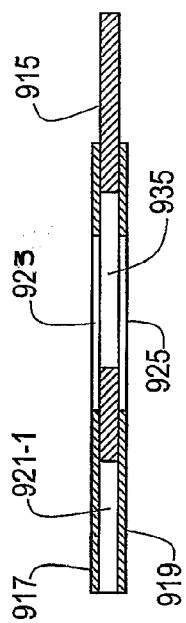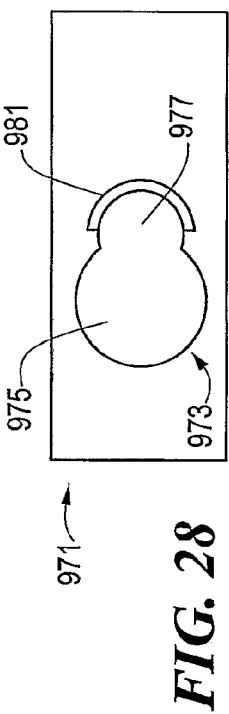

LOW PROFILE ADAPTOR FOR USE WITH A MEDICAL CATHETER

CROSS-REFERENCE TO RELATED APPLICATIONS

This is a Continuation of U.S. patent application Ser. No. 10/911,098 (now U.S. Pat. No. 7,641,648) filed Aug. 4, 2004, which is a Continuation of U.S. patent application Ser. No. 10/078,223 (now U.S. Pat. No. 6,802,836) filed Feb. 19, 2002, both of which applications are incorporated herein by reference in their entirety.

BACKGROUND OF THE INVENTION

The present invention relates generally to medical catheters, such as gastrostomy feeding tubes, and relates more particularly to low profile adaptors well-suited for use with medical catheters.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an entry site on the abdomen is identified and an incision can be made. A needle, with an outer cannula, is inserted through the entry site across the abdominal and gastric walls. While keeping the cannula in place, the needle is removed, and a flexible wire is passed through the cannula into the stomach and into a snare loop extended from the distal end of the endoscope. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled from its proximal end through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract. Additionally, a "Y-port" adapter is typically attached to the proximal end of the feeding tube, the Y-port adapter being adapted to receive a pair of connector tips through which food and/or medications may be dispensed. In addition, a detachable locking clip is typically secured to the feeding tube at a point between the external bolster and the Y-port adapter to prevent gastric fluids from escaping through the proximal end of the feeding tube when the feeding tube is not in use.

Alternative techniques for implanting gastrostomy feeding tubes using percutaneous endoscopic gastrostomy are disclosed in U.S. Pat. No. 5,112,310, inventor Grobe, which issued May 12, 1992, and U.S. Pat. No. 5,167,627, inventors Clegg et al., which issued Dec. 1, 1992, both of which are incorporated herein by reference.

Although gastrostomy feeding tubes of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. Consequently, a variety of low-profile replacement tube assemblies (also referred to in the art as low-profile replacement PEG devices) have been designed for implantation within the stoma tract following the removal of an initially-implanted gastrostomy feeding tube. Such replacement assemblies are referred to as being "low-profile" because they are considerably more compact externally than the above-described initially-implanted gastrostomy feeding tube assemblies.

An example of a low-profile replacement PEG device is disclosed in U.S. Pat. No. 4,944,732, inventor Russo, which issued Jul. 31, 1990, and which is incorporated herein by reference. The low-profile replacement PEG device of said patent comprises a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The device is adapted to be installed in a patient so that the tube portion extends through a pre-established stoma with the tip portion located in the patient's stomach and with the fitting portion and the flange portion engaging the skin of the patient adjacent the stoma.

The deformable tip portion of the above-described low-profile replacement PEG device functions as an internal bolster to anchor its associated tube portion in a patient's stomach. To implant and/or remove the aforementioned tube portion from a patient's stomach, an obturator or similar device is typically inserted through the tube portion and is used to elongate or otherwise deform the tip portion in such a way as to permit the tip portion to fit through the stoma. Removal of the obturator from the tip portion then permits the tip portion to expand to its original shape for anchoring.

Another type of low-profile replacement PEG device uses an inflatable balloon, instead of a deformable tip portion, as an internal bolster to retain the distal end of its associated tube within a patient's stomach. To implant such a device in a patient, the inflatable balloon is deflated, the distal end of the tube portion is inserted through the stoma, and the balloon is then inflated. To remove the implanted device from a patient, the balloon is deflated and the tube is then withdrawn from the stoma.

Further examples of low-profile replacement PEG devices are disclosed in U.S. Pat. No. 4,863,438, inventors Gauderer et al., which issued Sep. 5, 1989; and U.S. Pat. No. 5,720,734, inventors Copenhaver et al., which issued Feb. 24, 1998, both of which are incorporated herein by reference.

Although low-profile replacement PEG devices are less awkward and bulky than initially-implanted gastrostomy tube assemblies, the use of such low-profile replacement PEG devices suffers from its own set of shortcomings. One such shortcoming is that the implantation of a low-profile replacement PEG device must be preceded by the removal of an initially-implanted gastrostomy tube. Such removal typically involves pulling on the proximal end of the gastrostomy tube until the internal bolster fails and is drawn through the stoma. As can readily be appreciated, such a procedure can be quite painful to the patient and can result in damage to the stoma, thereby delaying when the replacement device can be implanted.

Another shortcoming of many low-profile replacement PEG devices is that such devices typically do not last as long as initially-implanted gastrostomy tube assemblies (most commonly due to failure of their internal anchoring mechanisms or due to clogging or other failure of their valve mechanisms) and, therefore, must be replaced more frequently than is the case with initially-implanted gastrostomy tube assemblies.

Still another shortcoming of many low-profile replacement PEG devices is that such devices are typically not adjustable in length. This can be problematic because there is often an appreciable variation in stoma length from patient to patient. Consequently, it is typically necessary, after removal of the initially-implanted tube and prior to implantation of the replacement device, to measure the length of the stoma and then to select a replacement device having an appropriate length. As can readily be appreciated, this approach requires that there be made available an inventory of replacement devices of varying lengths.

In order to avoid the aforementioned shortcomings of low-profile replacement PEG devices while, at the same time, avoiding the above-described problems associated with having a gastrostomy tube extend externally for a substantial length, there have recently been devised a number of adaptors designed for use in converting an initially-implanted gastrostomy tube into a low-profile PEG device. One such adaptor is disclosed in U.S. Pat. No. 5,549,657, inventors Stern et al., which issued Aug. 27, 1996, and which is incorporated herein by reference. According to said patent, an adaptor is disclosed therein that is designed for use with a gastostomy feeding tube which has been inserted by means of conventional endoscopic procedures and which has been cut to a desired length by a surgeon. The adaptor is said to comprise an anti-reflux valve assembly having a stem which can be plugged into the open end of the feeding tube. The valve assembly is said to contain a seal which functions as a one-way valve to prevent reflux of gastric contents but which permits the introduction of feeding solution into the feeding tube. A clamp is placed around the feeding tube and the valve stem and is locked into place to secure the valve assembly to the feeding tube at a location flush with the patient's skin. A silicone cover is placed around the clamp to protect the patient from skin irritation caused by the clamp and also to protect the clamp and valve assembly from contaminants.

Although the aforementioned adaptor favorably addresses some of the problems discussed above, the present inventors have identified certain shortcomings associated therewith. One such shortcoming is that the clamp of said adaptor is quite small and, therefore, difficult to manipulate. Another shortcoming is that the clamp has a tendency to pinch the proximal end of the gastrostomy tube at those points where the male and female sections of the clamp are joined. Such pinching, over time, has a tendency to cause the tube to tear. In addition, once the clamp is closed, it cannot be re-opened; consequently, one cannot remove and re-attach the valve stem and the clamp from the proximal end of the gastrostomy feeding tube. Accordingly, once the clamp has been closed, one cannot adjust the length of the gastrostomy feeding tube nor can one clean the valve stem or the proximal end of the feeding tube to remove any accumulated debris therewithin. Moreover, one cannot simply eliminate the clamp from the aforementioned adaptor since, in the absence of the clamp, the valve stem, which has a barb-type fitting, can rather easily be pulled out of the feeding tube (i.e., with about a 5 pound pulling force).

SUMMARY OF THE INVENTION

It is an object of the present invention to provide a novel low profile adaptor designed for use with a medical catheter, such as a gastrostomy feeding tube.

It is another object of the present invention to provide a low profile adaptor as described above that overcomes at least some of the problems described above in connection with existing PEG devices, in general, and low profile adaptors, in particular.

Therefore, according to one aspect of the invention, there is provided a low profile adaptor well-suited for use with a medical catheter, such as a gastrostomy feeding tube, said adaptor comprising (a) a first connector portion, said first connector portion being insertable into a first end of the medical catheter, said first connector portion comprising a first tubular member; and (b) a second connector portion, said second connector portion comprising a second tubular member, said second tubular member being directly engageable with said first tubular member.

In a preferred embodiment, the low profile adaptor comprises a lower connector portion, an upper connector portion and a valve. The lower connector portion comprises a tubular portion and an annular portion, the annular portion radially surrounding the tubular portion along an intermediate length thereof. A helical thread is formed on the inside surface of the tubular portion. A circular lip projects upwardly a short distance from the top surface of the annular portion. The upper connector portion comprises a tubular section adapted for insertion into the tubular portion of the lower connector portion. An external helical thread is formed on the tubular section of the upper connector portion for mating engagement with the thread on the interior of the tubular portion of the lower connector portion. The upper connector portion also includes an annular base. The top of the base is shaped to include a cavity for receiving the valve, the cavity being in fluid communication with the tubular section. A double-walled circular lip is formed on the bottom of the base, the double-walled lip being sized and shaped to define a groove adapted to matingly receive the lip on the upper connector portion. In use, the lower connector portion is inserted into the end of a catheter, and the tubular section of the upper connector portion is screwed into the tubular portion of the lower connector, with the catheter being ensnared between the lips of the upper and lower connector portions.

As can readily be appreciated, although the adaptor discussed above is described as being a low profile adaptor, such an adaptor is also suitable for use with medical catheters, such as gastrostomy feeding tubes, that extend externally for several inches. Accordingly, the adaptors of the present invention are not limited to being low profile adaptors.

According to another aspect of the invention, there is provided the combination of (a) a first medical catheter, said first medical catheter having a first bore; (b) a first connector portion, said first connector portion being inserted into a first end of said first medical catheter and having a second bore in fluid communication with said first bore; and (c) a second connector portion, said second connector portion being secured directly to said first connector portion and having a third bore in fluid communication with said second bore, with said first end of said first medical catheter being ensnared between said first connector portion and said second connector portion.

According to still another aspect of the invention, there is provided an assembly for restricting the diameter of a medical catheter, said assembly comprising (a) a first member, said first member being provided with a first transverse opening having a first area and a second area, said first area having a diameter greater than that of said medical catheter, said second area having a diameter less than that of said medical catheter; and (b) a second member, said second member being provided with a second transverse opening having a third area and a fourth area, said third area having a diameter greater than that of said medical catheter, said fourth area having a diameter less than that of said medical catheter; (c) wherein said first member and said second member are positionable relative to one another between a first position wherein said first area and said third area are aligned and a second position wherein said second area and said fourth area are aligned.

For purposes of the present specification and claims, relational terms like "top," "bottom," "upper," and "lower" are used to describe the present invention in a context in which the invention is secured to a catheter extending upwardly out of a patient. It is to be understood that, by orienting a patient such that the catheter extends outwardly in a direction other than upwardly, the directionality of the invention will need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 4 is an exploded section view of a second embodiment of a low profile adaptor constructed according to the teachings of the present invention for use with a gastrostomy feeding tube;

FIG. 5 is a section view of the low profile adaptor of FIG. 4, with the upper and lower portions of the connector being shown in a partially assembled state;

FIG. 6 is a section view of the low profile adaptor of FIG. 4, with the upper and lower portions of the connector being shown in a partially assembled state and with the proximal end of a gastrostomy feeding tube being shown inserted over the lower connector portion and partially inserted into the upper connector portion;

FIG. 7 is a section view of the low profile adaptor of FIG. 4, with the proximal end of a gastrostomy feeding tube being shown secured between the fully assembled upper and lower portions of the connector;

FIG. 24 is a top view of the assembly of FIG. 23 shown in its open position;

FIG. 25 is a section view of the assembly of FIG. 24 taken along lines 1-1;

FIG. 26 is a top view of the assembly of FIG. 23 shown in its closed position;

FIG. 27 is a section view of the assembly of FIG. 26 taken along lines 2-2; and

FIG. 28 is a top view of a modification of the slide shown in FIG. 23.

DETAILED DESCRIPTION OF PREFERRED EMBODIMENTS

Figure 1:
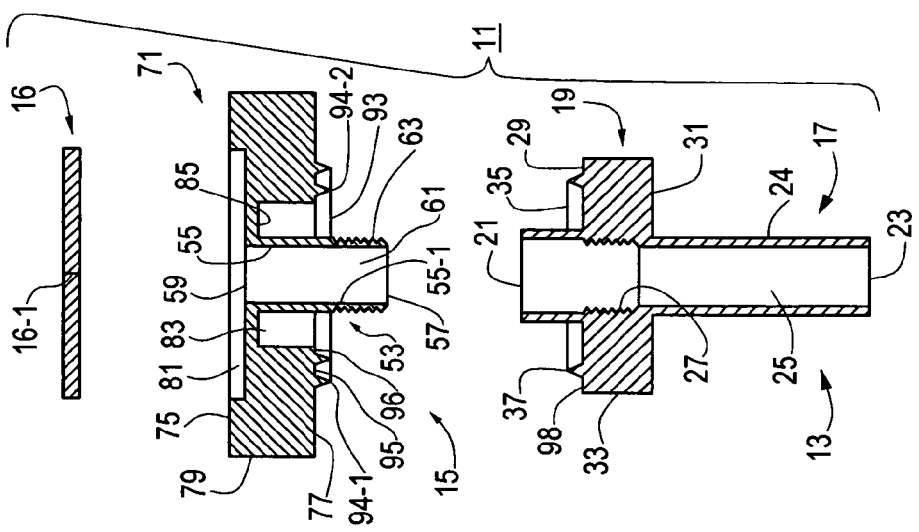
FIG. 1 is an exploded section view of a first embodiment of a low profile adaptor constructed according to the teachings of the present invention for use with a gastrostomy feeding tube.

Referring now to FIG. 1, there is shown an exploded section view of a first embodiment of a low profile adaptor constructed according to the teachings of the present invention for use with a gastrostomy feeding tube, said low profile adaptor being identified generally by reference numeral 11.

Adaptor 11 comprises a lower connector portion 13, an upper connector portion 15 and a valve 16.

Lower connector portion 13, which is a unitary structure preferably made of molded medical grade plastic, comprises a tubular portion 17 and an annular portion 19, annular portion 19 radially surrounding tubular portion 17 along an intermediate length thereof. Tubular portion 17 is shaped to include an open top end 21, an open bottom end 23, a circular wall 24, and a longitudinal bore 25. A helical thread 27 is formed on the inside surface of wall 24 along that portion of its length surrounded by annular portion 19.

Annular portion 19 is shaped to include a top surface 29, a bottom surface 31, and an outer surface 33. A circular lip 35, which is spaced inwardly from outer surface 33 and is concentrically positioned around tubular portion 17, projects upwardly a short distance from top surface 29. For reasons to become apparent below, lip 35 is generally triangular in longitudinal cross-section and tapers upwardly in thickness until coming to a point 37 at its top.

Upper connector portion 15, which is a unitary structure preferably made of molded medical grade plastic, comprises a tubular section 53. Tubular section 53 is shaped to define a circular side wall 55, an open bottom end 57, an open top end 59, and a longitudinal bore 61. The bottom portion 55-1 of circular side wall 55 has a slightly smaller outer diameter than the remainder of side wall 55. An external helical thread 63 is formed on the outer surface of bottom portion 55-1 of side wall 55. As will be discussed below in greater detail, tubular section 53 is adapted for insertion through open top end 21 and into tubular portion 17 of lower connector portion 13, with thread 63 of bottom portion 55-1 matingly engaging thread 27.

Upper connector portion 15 further comprises a base section 71. Base section 71 is generally annular in shape and includes a top surface 75, a bottom surface 77, and an outer surface 79. A centrally disposed cavity 81, the purpose of which will be described below, is circular in shape and extends downwardly a short distance from top surface 75. An annular cavity 83, the purpose of which will also be described below, surrounds tubular section 53 and extends upwardly a short distance from bottom surface 77, cavity 83 being smaller in diameter than cavity 81 and being separated therefrom by a wall 85. Tubular section 53 extends downwardly from wall 85, with open top end 59 of tubular section 53 serving as an aperture to interconnect cavity 81 and bore 61.

A double-walled circular lip 93 is formed on bottom surface 77 and extends downwardly therefrom a short distance, lip 93 being concentrically spaced inwardly a short distance from outer surface 79. For reasons to become apparent below, lip 93 is sized and shaped to define a groove 95 that is generally complementary in size and shape to lip 35. In addition, lip 93 tapers downwardly in thickness until coming to a pair of points 94-1 and 94-2 at its bottom.

It should be understood that, although base section 71 is described in the present embodiment as being annular, base section 71 could take a variety of shapes including, but not limited to, a correspondingly apertured rectangular or triangular shape. However, regardless of its shape, base section 71 should be sized so as to be larger than the entry site of the gastrostomy feeding tube implanted in the patient in order to prevent the tube and adaptor 11 from being inadvertently drawn into the body of the patient.

It should also be understood that, although lower connector portion 13 and upper connector portion 15 are secured to one another in the present embodiment by threads 63 and 27, lower connector portion 13 and upper connector portion 15 could alternatively be secured to one another by a snap fit, a slide fit or other suitable means.

Valve 16, which may be, for example, a silicone gasket of the type disclosed in U.S. Pat. No. 5,549,657, is seated in cavity 81 and may be held in place there by a ring (not shown) that is bonded to base section 71. Valve 16 is provided with a slit 16-1 that permits a cannula (not shown) to be inserted therethrough so that foods and/or medications may be delivered to a patient but that also stops the upward flow of gastric fluids from the patient when said cannula is not inserted through slit 16-1.

Figure 3:
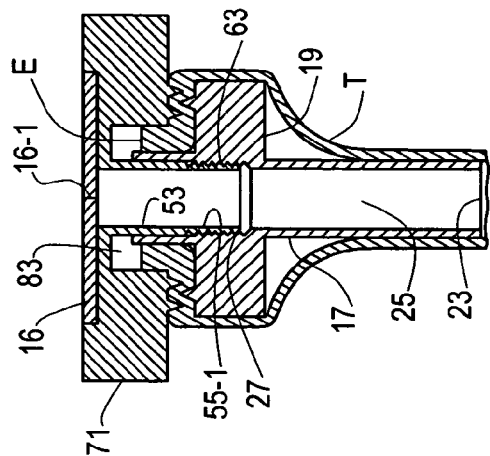
FIG. 3 is a section view of the low profile adaptor of FIG. 1, with the proximal end of a gastrostomy feeding tube being shown secured between the fully assembled upper and lower portions of the connector.
Figure 2:
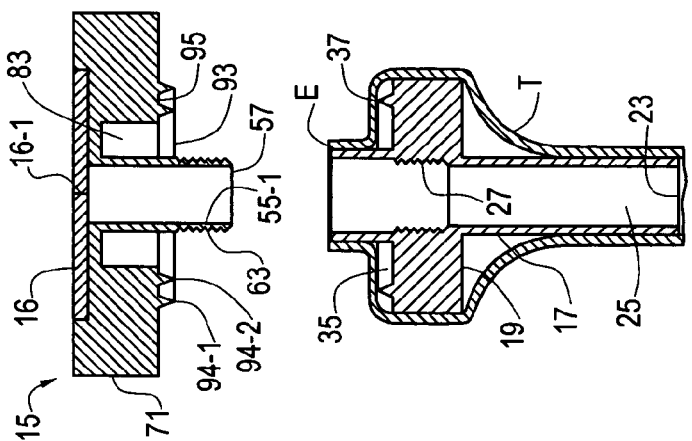
FIG. 2 is a partially exploded section view of the low profile adaptor of FIG. 1, with the lower portion of the connector being shown inserted into the proximal end of a gastrostomy feeding tube.

Referring now to FIGS. 2 and 3, there is illustrated the manner in which adaptor 11 may be secured to the proximal end E of an implanted gastrostomy feeding tube T. First, as seen in FIG. 2, proximal end E of tube T is inserted over the entirety of lower connector portion 13, with bore 25 of lower connector portion 13 being oriented parallel to the length of tube T. As can readily be appreciated, lower connector portion 13 must be appropriately sized relative to tube T so that tube T can be stretched thereover in this manner.

Next, as seen in FIG. 3, bottom portion 55-1 of tubular section 53 is inserted down through end 21 of lower connector portion 13 and is then screwed, clockwise, until thread 63 fully engages thread 27. As lower connector portion 13 and upper connector portion 15 are initially brought together, lip 35 is drawn into groove 95, trapping tube T therebetween. The drawing together of lower connector portion 13 and upper connector portion 15 in the aforementioned manner also causes the proximal end E of tube T to be forced up into cavity 83. As can readily be appreciated, by providing a space into which the proximal end E of tube T can be tucked, cavity 83 permits portions 13 and 15 to be drawn closer together than they otherwise would be permitted to be drawn. Continued clockwise rotation of upper connector portion 15 relative to lower connector portion 13 increases the retentive force of adaptor 11 against tube T. Specifically, as upper connector portion 15 is tightened onto lower connector portion 13, points 37, 94-1 and 94-2 all engage tube T. In addition, as upper connector portion 15 is tightened onto lower connector portion 13, a first right angle pinch point is formed in tube T by corner 96 (see FIG. 1) of base section 71, and a second right angle pinch point is formed in tube T by corner 98 (see FIG. 1) of intermediate section 17. Each of said two pinch points extends 360 degrees around tube T.

With tube T wedged between lower connector portion 13 and upper connector portion 15 in the above-described manner, adaptor 11 has a retentive force, or grip strength, on tube T of approximately 18 pounds, which is more than three times greater than the force typically exerted by a barb-type fitting.

It should be noted that, to loosen adaptor 11 from a tube T to which it has been attached or to attach adaptor 11 to an unattached tube T, upper connector portion 15 must be rotated relative to lower connector portion 13. This requires that an operator keep lower connector portion 13 stationary while rotating connector portion 15; accordingly, to tighten or to loosen adaptor 11, the operator will typically need to use two hands, one for connector portion 13 and the other for connector portion 15. Consequently, because the lower connector portion 13 is not typically accessible for manipulation when adaptor 11 is installed on a patient in a low profile orientation, but rather, requires that adaptor 11 be pulled away from the abdomen to reveal lower connector portion 13, the present invention reduces the likelihood that a patient will inadvertently loosen adaptor 11.

As can be appreciated, adaptor 11 possesses a number of significant features, some of which are not possessed by existing adaptors for gastrostomy feeding tubes. One such feature is that adaptor 11 is secured to the gastrostomy feeding tube in a 360 degree manner. This minimizes the chance that an uneven distribution of retentive force will be applied to the tube, causing the tube to tear. Another such feature is that adaptor 11 is capable of being detached from and then re-attached to the tube, thereby permitting the length of the tube to be adjusted and/or permitting the adaptor and tube to be cleaned of debris. Still another feature, noted above, is that adaptor 11 retains the tube with a considerable retentive force. Specifically, adaptor 11 is able to withstand a pulling force of approximately 18 pounds without compromising the quality of the seal between the tube and the adaptor 11. Still yet another feature is that adaptor 11 is easy to operate.

Although adaptor 11 is designed primarily for low profile use with a gastrostomy feeding tube, it should be understood that adaptor 11 is not limited to low profile use and could be used with a gastrostomy feeding tube in a high profile arrangement. Moreover, apart from whether adaptor is used in a low profile or high profile context, adaptor 11 is not limited to use with gastrostomy feeding tubes and may be used with various other medical catheters.

Referring now to FIG. 4, there is shown an exploded section view of a second embodiment of a low profile adaptor constructed according to the teachings of the present invention for use with a gastrostomy feeding tube, said adaptor being identified generally by reference numeral 111.

Adaptor 111 is similar in most respects to adaptor 11, the principal differences between adaptor 111 and adaptor 11 being that (i) adaptor 111 has a lower profile than does adaptor 11 and (ii) the tubular portion of the lower connector portion of adaptor 111 does not extend upwardly beyond the annular portion of the lower connector portion of adaptor 111.

More specifically, adaptor 111 comprises a lower connector portion 113, an upper connector portion 115 and a valve 116.

Lower connector portion 113, which is a unitary structure preferably made of molded medical grade plastic, comprises a tubular section 117. Tubular section 117 is shaped to include an open top end 119, an open bottom end 121, a circular wall 123, and a longitudinal bore 125. A helical thread 127, which extends downwardly a short distance from open top end 119, is formed on the inside surface of wall 123.

Lower connector portion 113 also comprises an annular wall 129, annular wall 129 radially surrounding tubular section 117 at its top end. Annular wall 129 is shaped to include a top surface 131, a bottom surface 133, and an outer surface 135. A circular lip 137 is formed on top surface 131 and extends upwardly therefrom a short distance, lip 137 being concentrically spaced inwardly a short distance from outer surface 135. Lip 137 is generally triangular in longitudinal cross-section and tapers upwardly in thickness until coming to a point 139 at its top.

Upper connector portion 115, which is a unitary structure preferably made of molded medical grade plastic, comprises a tubular section 153. Tubular section 153 is shaped to define a circular side wall 155, an open bottom end 157, an open top end 159, and a longitudinal bore 161. The bottom portion 155-1 of circular side wall 155 has a slightly smaller outer diameter than the remainder of side wall 155. An external helical thread 163 is formed on the outer surface of bottom portion 155-1 of side wall 155. As will be discussed below in greater detail, tubular section 153 is adapted for insertion into bore 125 of lower connector portion 113, with thread 163 of bottom portion 155-1 matingly engaging thread 127.

Upper connector portion 115 further comprises a base section 171, base section 171 differing from base section 71 only in its reduced thickness. Accordingly, base section 171 is generally annular in shape and includes a top surface 175, a bottom surface 177, and an outer surface 179. A centrally disposed cavity 181, the purpose of which will be described below, is circular in shape and extends downwardly a short distance from top surface 175. An annular cavity 183, the purpose of which will also be described below, concentrically surrounds tubular section 153 and extends upwardly a short distance from bottom surface 177, second cavity 183 being smaller in diameter than first cavity 181 and being separated therefrom by a wall 185. Tubular section 153 is centrally disposed within cavity 183 and extends downwardly from wall 185, with open top end 159 of tubular section 153 serving as an aperture to interconnect cavity 181 and bore 161.

A double-walled circular lip 193 is formed on bottom surface 177 and extends downwardly therefrom a short distance, lip 193 being concentrically spaced inwardly a short distance from outer surface 179. For reasons to become apparent below, lip 193 is sized and shaped to define a groove 195 that is generally complementary in size and shape to lip 137. In addition, lip 193 tapers downwardly in thickness until coming to a pair of points 194-1 and 194-2 at its bottom.

It should be understood that, although base section 171 is described in the present embodiment as being annular, base section 171 could take a variety of shapes including, but not limited to, a correspondingly apertured rectangular or triangular shape. However, regardless of its shape, base section 171 should be sized so as to be larger than the entry site of the gastrostomy feeding tube implanted in the patient in order to prevent the tube and adaptor 111 from being inadvertently drawn into the body of the patient.

It should also be understood that, although lower connector portion 113 and upper connector portion 115 are secured to one another in the present embodiment by threads 163 and 127, lower connector portion 113 and upper connector portion 115 could alternatively be secured to one another by a snap fit, a slide fit or other suitable means.

Valve 116, which may be identical to valve 16 is seated in cavity 181 and may be held in place there by a ring (not shown) that is bonded to base section 171. Valve 116 is provided with a slit 116-1 that permits a cannula (not shown) to be inserted therethrough so that foods and/or medications may be delivered to a patient but that also stops the upward flow of gastric fluids from the patient when said cannula is not inserted through slit 116-1.

Adaptor 111 is not limited to low profile use nor is it limited to use with gastrostomy feeding tubes.

Referring now to FIGS. 5 through 7, there is shown the manner in which adaptor 111 may be attached to the proximal end E of a gastrostomy feeding tube T. First, as seen in FIG. 5, lower connector portion 113 and upper connector portion 115 are partially assembled by screwing tubular member 153 of upper connector portion 115 partially into bore 125 of lower connector portion 113. For reasons to become apparent below, tubular member 153 is not screwed completely into bore 125, and a space is left between lip 137 of lower connector portion 113 and lip 193 of upper connector portion 115.

Next, as seen in FIG. 6, the proximal end E of a tube T is inserted over lower connector portion 113 and is passed (preferably as far up as possible) into cavity 183 of upper connector portion 115. Finally, as seen in FIG. 7, upper connector portion 115 is screwed completely into lower connector portion 113, thereby ensnaring the proximal end E of tube T therebetween. Specifically, as upper connector portion 115 is tightened onto lower connector portion 113, tube T is compressed between lip 193 of upper connector portion 115 and lip 137 of lower connector portion 113, with points 139, 194-1 and 194-2 all digging into and engaging tube T. In addition, the above-described tightening together of lower connector portion 113 and upper connector portion 115 results in the formation of a pair of right angle pinch points in tube T analogous to those formed by adaptor 11.

It should be noted that, by partially assembling adaptor 111 in the above-described manner before inserting a tube thereover, the handling of adaptor 111 and the connection of a tube thereto by a physician is facilitated.

Figure 8:
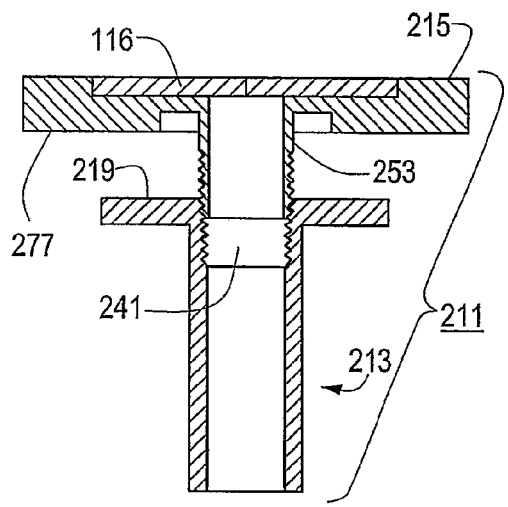
FIG. 8 is a section view of a third embodiment of a low profile adaptor constructed according to the teachings of the present invention for use with a gastrostomy feeding tube, the upper and lower portions of the connector being shown in a partially assembled state.

Referring now to FIG. 8, there is shown a section view of a third embodiment of a low profile adaptor constructed according to the teachings of the present invention for use with a gastrostomy feeding tube, said adaptor being shown in a partially assembled state and being identified generally by reference numeral 211.

Adaptor 211 is similar in most respects to adaptor 111, the principal differences between adaptor 211 and adaptor 111 being that adaptor 211 does not include an upwardly projecting lip, like lip 137, on its lower connector portion 213 or a downwardly projecting lip, like lip 193, on its upper connector portion 215.

Figure 9:
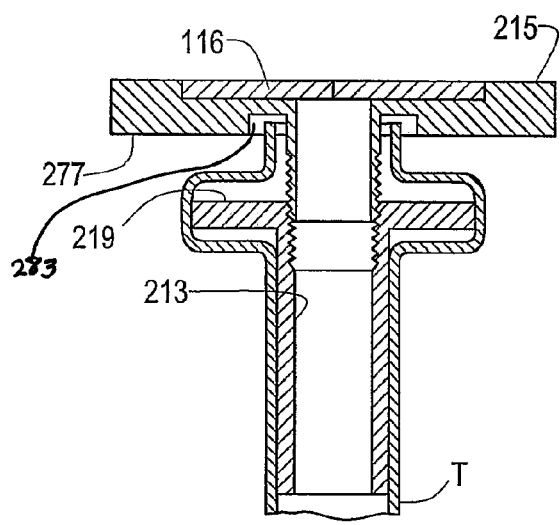
FIG. 9 is a section view of the low profile adaptor of FIG. 8, with the upper and lower portions of the connector being shown in a partially assembled state and with the proximal end of a gastrostomy feeding tube being shown inserted over the lower connector portion and partially inserted into the upper connector portion.
Figure 10:
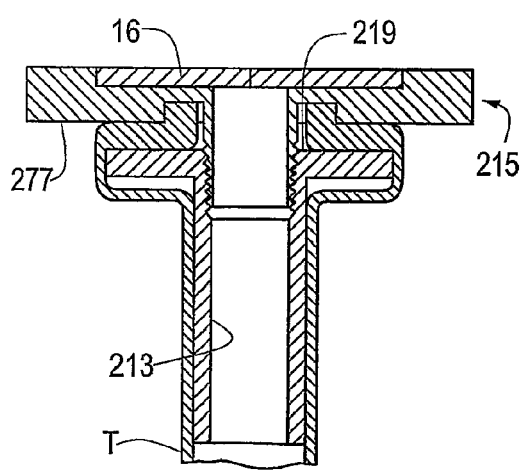
FIG. 10 is a section view of the low profile adaptor of FIG. 8, with the proximal end of a gastrostomy feeding tube being shown secured between the fully assembled upper and lower portions of the connector.

The manner in which adaptor 211 may be attached to the proximal end E of a gastrostomy feeding tube T is shown in FIGS. 8 through 10. First, as shown in FIG. 8, lower connector portion 213 and upper connector portion 215 are partially assembled by screwing tubular member 253 of upper connector portion 215 partially into bore 241 of lower connector portion 213. Next, as seen in FIG. 9, the proximal end E of a tube T is inserted over lower connector portion 213 and is passed (preferably as far up as possible) into cavity 283 of upper connector portion 215. Next, as seen in FIG. 10, upper connector portion 215 is screwed completely into lower connector portion 213, thereby trapping the proximal end E of tube T therebetween. Specifically, as upper connector portion 215 is tightened onto lower connector portion 213, tube T is compressed between lower surface 277 of upper connector portion 215 and upper surface 219 of lower connector portion 213. In addition, the above-described tightening together of lower connector portion 213 and upper connector portion 215 results in the formation of a pair of right angle pinch points in tube T analogous to those formed by adaptor 111.

Adaptor 211 is not limited to low profile use nor is it limited to use with gastrostomy feeding tubes.

Figure 11:
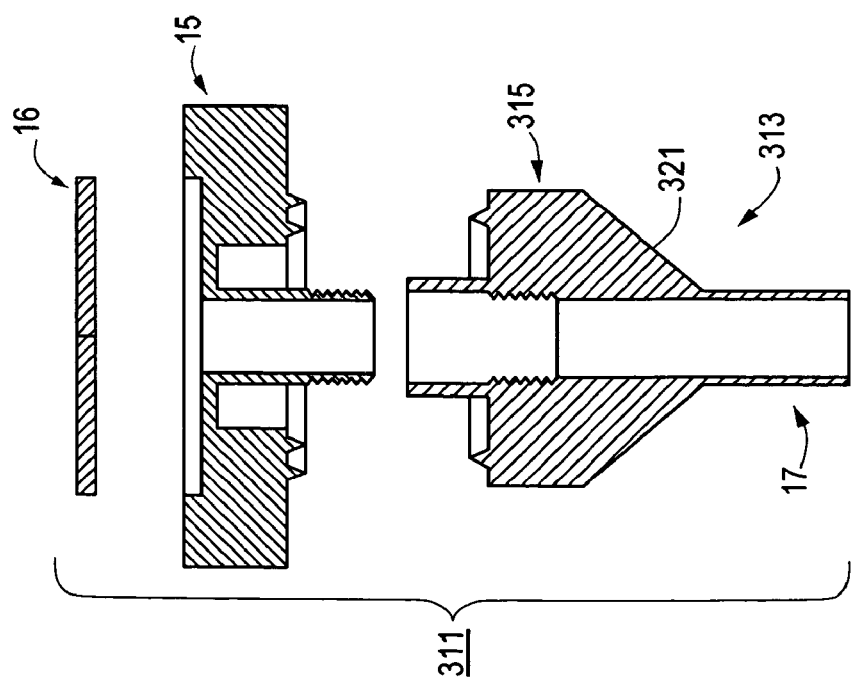
FIG. 11 is an exploded section view of a fourth embodiment of a low profile adaptor constructed according to the teachings of the present invention for use with a gastrostomy feeding tube.

Referring now to FIG. 11, there is shown an exploded section view of a fourth embodiment of a low profile adaptor constructed according to the teachings of the present invention for use with a gastrostomy feeding tube, said low profile adaptor being identified generally by reference numeral 311.

Adaptor 311 is similar in virtually all respects to adaptor 11, the only difference between the two adaptors being that adaptor 311 includes a lower connector portion 313, instead of lower connector portion 13. Lower connector portion 313 differs from lower connector portion 13 in that lower connector portion 313 comprises an annular portion 315, instead of annular portion 19, annular portion 315 having a sloped bottom surface 321 to facilitate the insertion of a gastrostomy feeding tube thereover.

Adaptor 311 is not limited to low profile use nor is it limited to use with gastrostomy feeding tubes.

Figure 12:
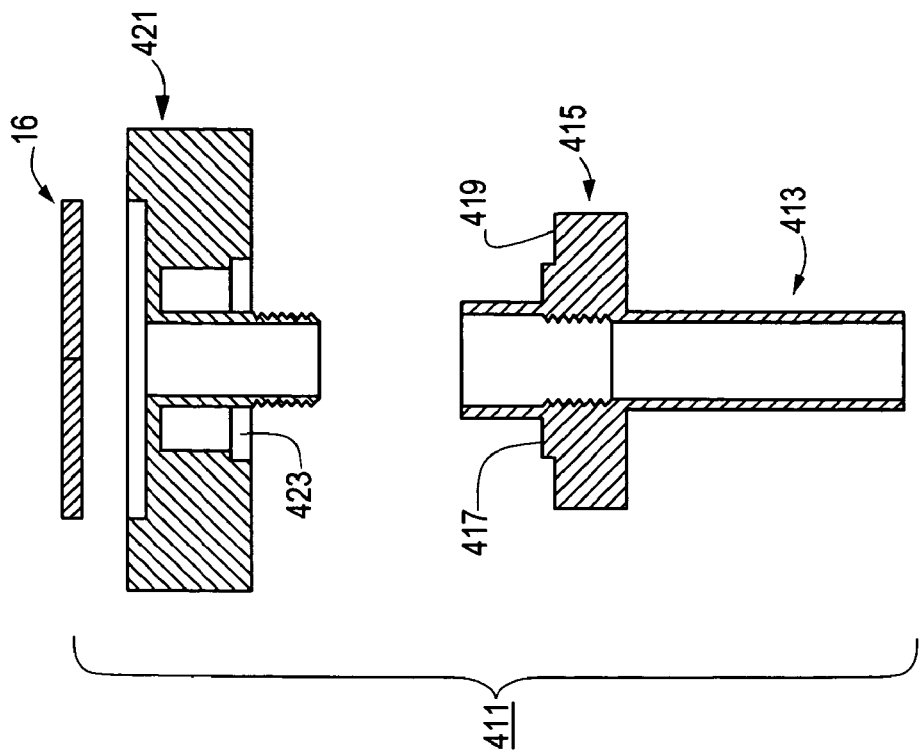
FIG. 12 is an exploded section view of a fifth embodiment of a low profile adaptor constructed according to the teachings of the present invention for use with a gastrostomy feeding tube.

Referring now to FIG. 12, there is shown an exploded section view of a fifth embodiment of a low profile adaptor constructed according to the teachings of the present invention for use with a gastrostomy feeding tube, said low profile adaptor being identified generally by reference numeral 411.

Adaptor 411 is similar in many respects to adaptor 11. One difference between adaptor 411 and adaptor 11 is that adaptor 411 comprises a lower connector portion 413, instead of lower connector portion 13. Lower connector portion 413 differs from lower connector portion 13 in that lower connector portion 413 does not include an annular portion having a lip 27, but instead, includes an annular portion 415 having an annular step 417 projecting upwardly from its top surface 419. Another difference between adaptor 411 and adaptor 11 is that adaptor 411 comprises an upper connector portion 421, instead of upper connector portion 15. Upper connector portion 421 differs from upper connector portion 15 in that upper connector portion 421 does not include a lip 93, but instead, is shaped to define an annular recess 423 adapted to receive step 417 of lower connector portion 413.

Adaptor 411 is not limited to low profile use nor is it limited to use with gastrostomy feeding tubes.

Figure 13:
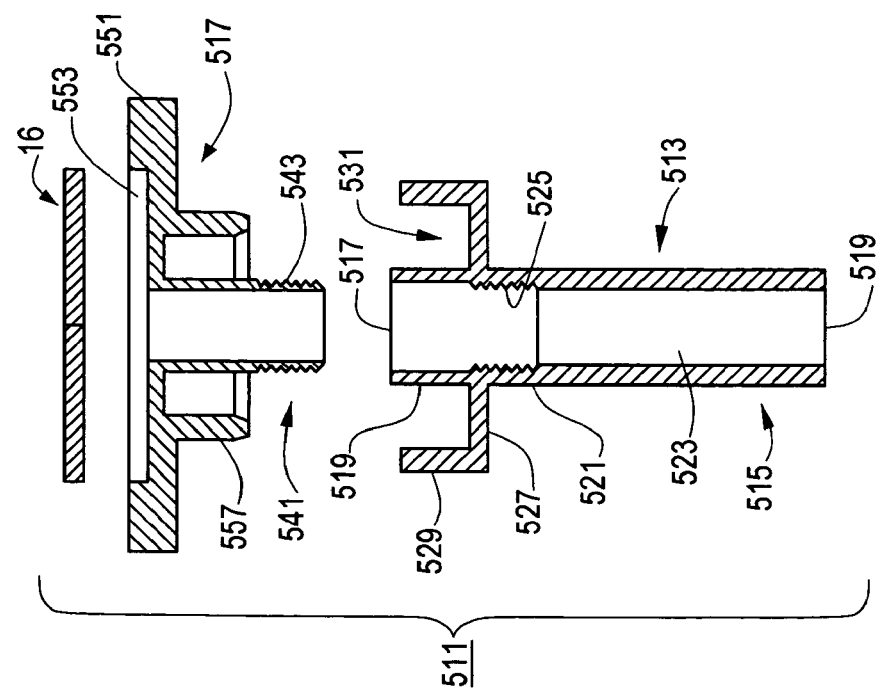
FIG. 13 is an exploded section view of a sixth embodiment of a low profile adaptor constructed according to the teachings of the present invention for use with a gastrostomy feeding tube.

Referring now to FIG. 13, there is shown an exploded section view of a sixth embodiment of a low profile adaptor constructed according to the teachings of the present invention for use with a gastrostomy feeding tube, said low profile adaptor being identified generally by reference numeral 511.

Adaptor 511, which is similar in certain respects to adaptor 11, comprises a lower connector portion 513, an upper connector portion 517 and valve 16.

Lower connector portion 513, which is a unitary structure preferably made of molded medical grade plastic, comprises a tubular portion 515, tubular portion 515 being shaped to include an open top end 517, an open bottom end 519, a circular side wall 521 and a longitudinal bore 523. A helical thread 525 is formed on the inside surface of wall 521 along an intermediate length thereof.

Lower connector portion 513 also comprises an annular portion surrounding tubular portion 515 at the top end thereof, said annular portion comprising a circumferential flange 527 formed on the outside surface of wall 521 and extending radially outwardly therefrom. An upwardly extending wall 529 is perpendicularly formed at the periphery of flange 527. Wall 529, flange 527 and upper section 519 jointly define an annular groove 531.

Upper connector portion 517, which is a unitary structure preferably made of molded medical grade plastic, comprises an open-ended tubular member 541 adapted for downward insertion into tubular portion 515 through top end 517. The bottom portion of tubular member 541 has a slightly smaller outer diameter than the remainder of tubular member 541. An external helical thread 543 is formed on the outer surface of the bottom portion of tubular member 541 to matingly engage thread 525.

Upper connector portion 517 further comprises a base section 551. A circular cavity 553, which is adapted to receive valve 16, is formed in base section 551 and extends downwardly a short distance from the top surface thereof. Cavity 553 is in fluid communication with tubular member 541 through the open top end of tubular member 541. A sleeve 557 is formed on base section 551 and extends downwardly a short distance from the bottom surface thereof. Sleeve 557 is appropriately dimensioned so that when tubular member 541 is inserted into the tubular member of lower connector portion 513, sleeve 557 is received within groove 531. In this manner, when the proximal end of a tube is inserted over lower connector portion 513 and upper connector portion 517 is then screwed into lower connector portion 513, the proximal end of the tube is forced up into sleeve 557, with wall 529 and sleeve 557 creating a plurality of pinch points in the tube.

Adaptor 511 is not limited to low profile use nor is it limited to use with gastrostomy feeding tubes.

Figure 14:
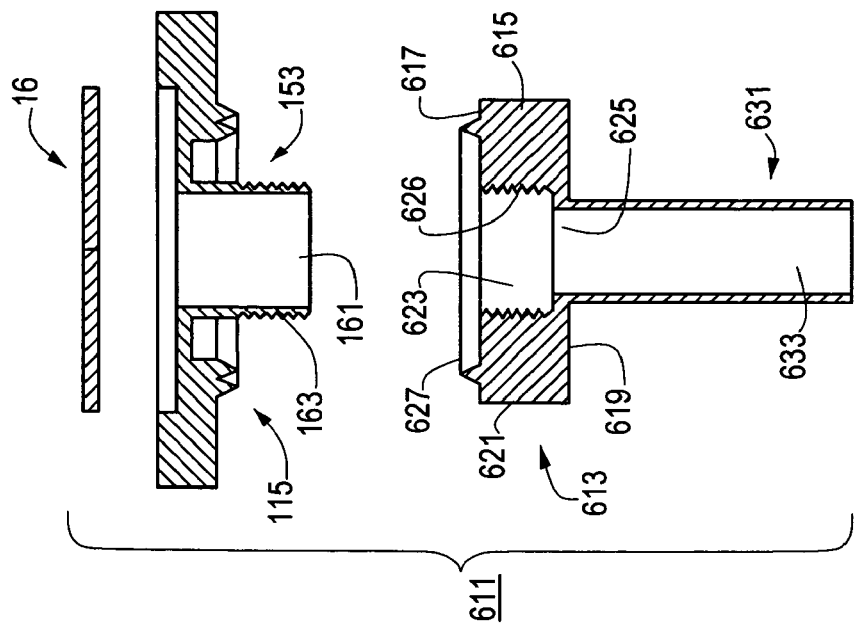
FIG. 14 is an exploded section view of a seventh embodiment of a low profile adaptor constructed according to the teachings of the present invention for use with a gastrostomy feeding tube.

Referring now to FIG. 14, there is shown an exploded section view of a seventh embodiment of a low profile adaptor constructed according to the teachings of the present invention for use with a gastrostomy feeding tube, said low profile adaptor being identified generally by reference numeral 611.

Adaptor 611 is similar in many respects to adaptor 11, the principal difference between the two adaptors being that adaptor 611 includes a lower connector portion 613, instead of lower connector portion 13.

Lower connector portion 613 comprises an annular base 615, base 615 having a top surface 617, a bottom surface 619, an outer wall 621 and a central bore. The upper portion 623 of said central bore has a greater diameter than the lower portion 625 thereof so that, when tubular member 153 of upper connector portion 115 is inserted into said bore, bore 161 of upper connector portion 115 has a diameter equal to or greater than the diameter of lower portion 625. A helical thread 626 is formed on the inside wall of upper portion 623 to matingly engage thread 163. A circular lip 627, identical in shape to lip 127, is formed on top surface 617 of base 615.

Lower connector portion 613 also comprises an open-ended tubular member 631. Tubular member 631, which extends downwardly from base 615, has a bore 633 that is aligned with lower portion 625 of the central bore of base 615 and is equal in diameter thereto.

Adaptor 611 is not limited to low profile use nor is it limited to use with gastrostomy feeding tubes.

Figure 15:
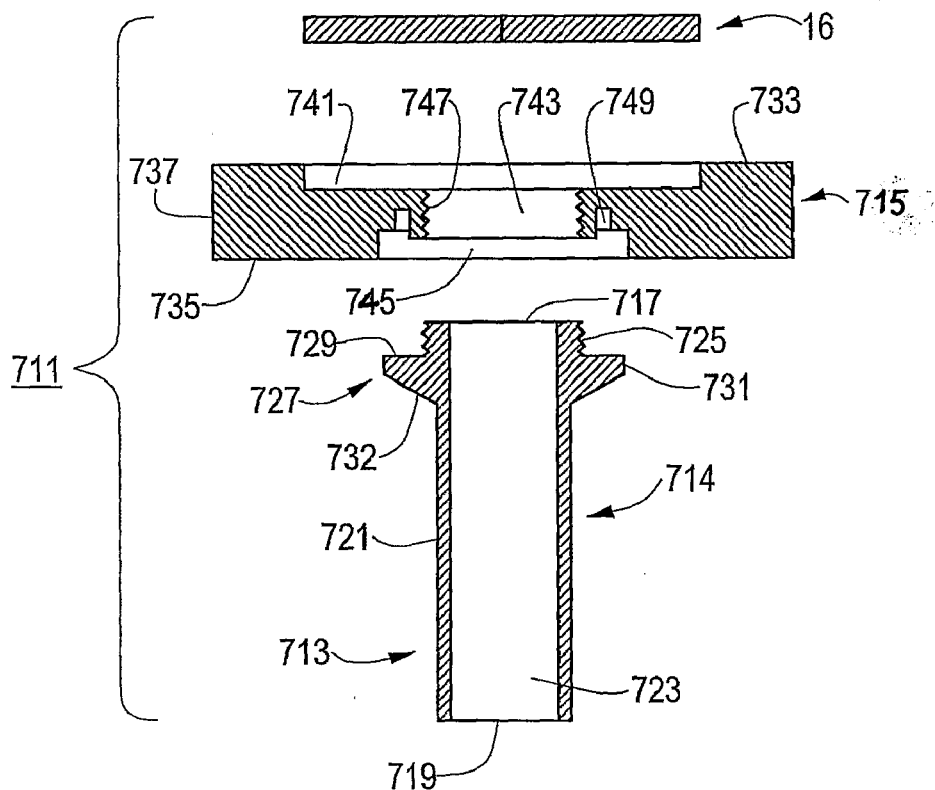
FIG. 15 is an exploded section view of an eighth embodiment of a low profile adaptor constructed according to the teachings of the present invention for use with a gastrostomy feeding tube.

Referring now to FIG. 15, there is shown an exploded perspective view of an eighth embodiment of a low profile adaptor constructed according to the teachings of the present invention for use with a gastrostomy feeding tube, said low profile adaptor being identified generally by reference numeral 711.

Adaptor 711 comprises a lower connector portion 713, an upper connector portion 715 and a valve 16.

Lower connector portion 713, which is a unitary structure preferably made of molded medical grade plastic, comprises a tubular portion 714 having an open top end 717, an open bottom end 719, a circular wall 721 and a longitudinal bore 723. A helical thread 725 is externally provided on wall 721 and extends downwardly a short distance from top end 717.

Lower connector portion 713 also comprises an annular flange 727, flange 727 surrounding tubular portion 714 just below the bottom of thread 725. Flange 727 is shaped to include a horizontal top surface 729, a vertical side surface 731 and a sloped bottom surface 732.

Upper connector portion 715, which is a unitary structure preferably made of molded medical grade plastic, comprises a top surface 733, a bottom surface 735, an outer surface 737 and a central bore. Said central bore is shaped to include a top section 741, an intermediate section 743, and a lower section 745. Top section 741 is appropriately dimensioned to receive valve 16. Intermediate section 743 and lower section 745 are appropriately dimensioned to receive the top portion of lower connector portion 713, and a helical thread 747 is formed on the inside surface of intermediate section 743 to matingly engage thread 725. An annular recess 749 is provided in upper connector portion 715 to receive the proximal end of a tube.

It should be noted that one distinction between adaptor 711 and adaptor 11 is that, whereas adaptor 11 comprises a lower connector portion 13 having a female thread 31 and an upper connector portion 15 having a male thread 63, adaptor 711 comprises a lower connector portion 713 having a male thread 725 and an upper connector portion 715 having a female thread 747.

Figure 16:
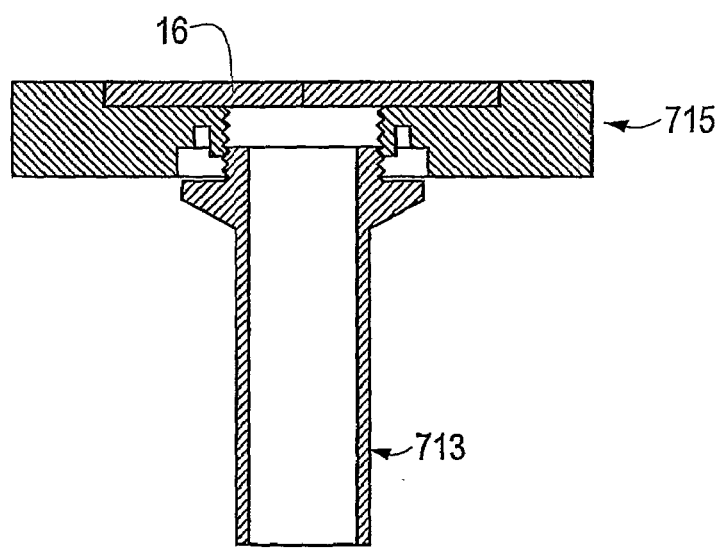
FIG. 16 is a section view of the low profile adaptor of FIG. 15, with the upper and lower portions of the connector being shown in a partially assembled state.
Figure 17:
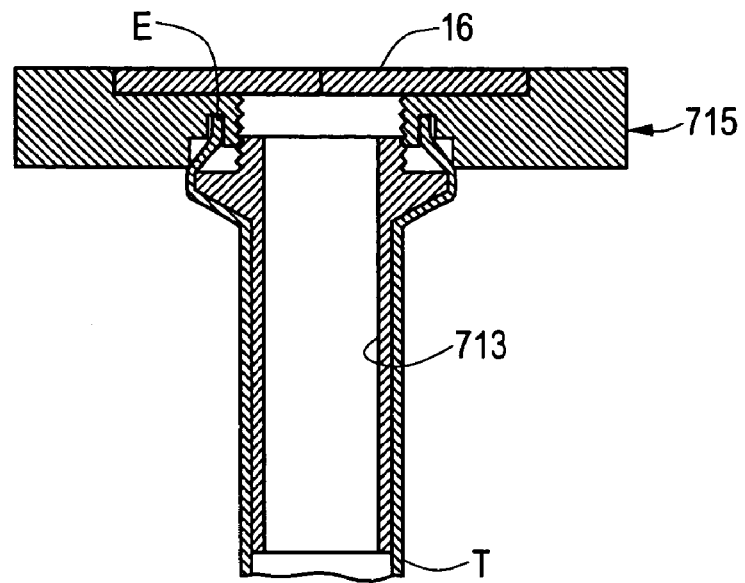
FIG. 17 is a section view of the low profile adaptor of FIG. 15, with the upper and lower portions of the connector being shown in a partially assembled state and with the proximal end of a gastrostomy feeding tube being shown inserted over the lower connector portion and partially inserted into the upper connector portion.
Figure 18:
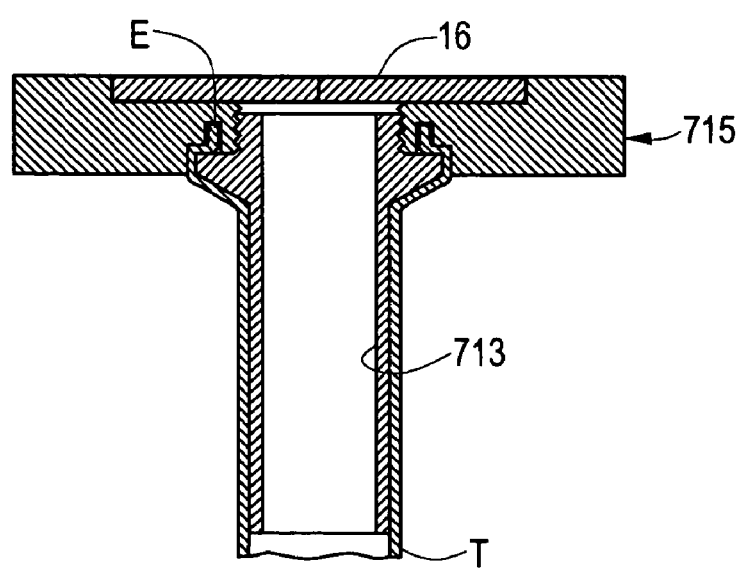
FIG. 18 is a section view of the low profile adaptor of FIG. 15, with the proximal end of a gastrostomy feeding tube being shown secured between the fully assembled upper and lower portions of the connector.

Referring now to FIGS. 16 through 18, there is shown the manner in which adaptor 711 may be secured to the proximal end E of a gastrostomy feeding tube T. First, as seen in FIG. 16, lower connector portion 713 is partially inserted and screwed into upper connector portion 715. Next, as seen in FIG. 17, the proximal end E of a tube T is inserted over lower connector portion 715 and is fed into recess 749 of upper connector portion 715. Lastly, as seen in FIG. 18, lower connector portion 713 is fully screwed into upper connector portion 715, ensnaring the proximal end E of tube T therebetween.

Adaptor 711 is not limited to low profile use nor is it limited to use with gastrostomy feeding tubes.

Figure 19:
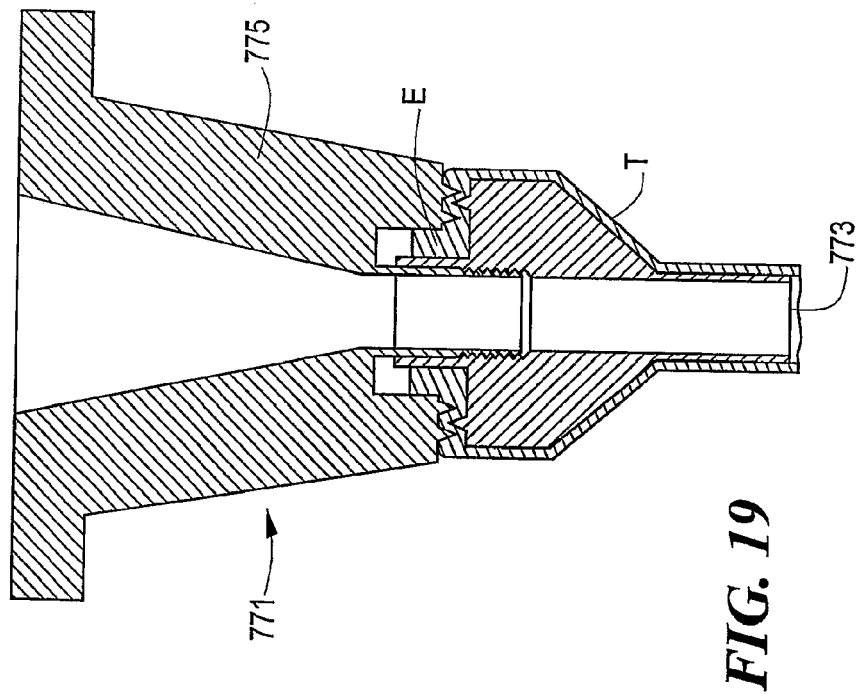
FIG. 19 is a section view of a ninth embodiment of a low profile adaptor constructed according to the teachings of the present invention, the low profile adaptor being shown attached to the proximal end of a gastrostomy feeding tube.

Referring now to FIG. 19, there is shown a section view of a ninth embodiment of a low profile adaptor constructed according to the teachings of the present invention, said low profile adaptor being shown attached to the proximal end E of a gastrostomy feeding tube T and being represented generally by reference numeral 771.

Adaptor 771 comprises a lower connector portion 773 and an upper connector portion 775. Lower connector portion 773 is identical to lower connector portion 313 of adaptor 311. Upper connector portion 775 is similar in certain respects to upper connector portion 15 of adaptor 311, upper connector portion 775 principally differing from upper connector portion 15 in that upper connector portion 775 is sized and shaped to receive a medical luer. Upper connector portion 775 additionally differs from upper connector portion 15 in that upper connector portion 775 is not shaped to include a cavity for receiving a valve 16.

Adaptor 771 is not limited to low profile use nor is it limited to use with gastrostomy feeding tubes.

Figure 20:
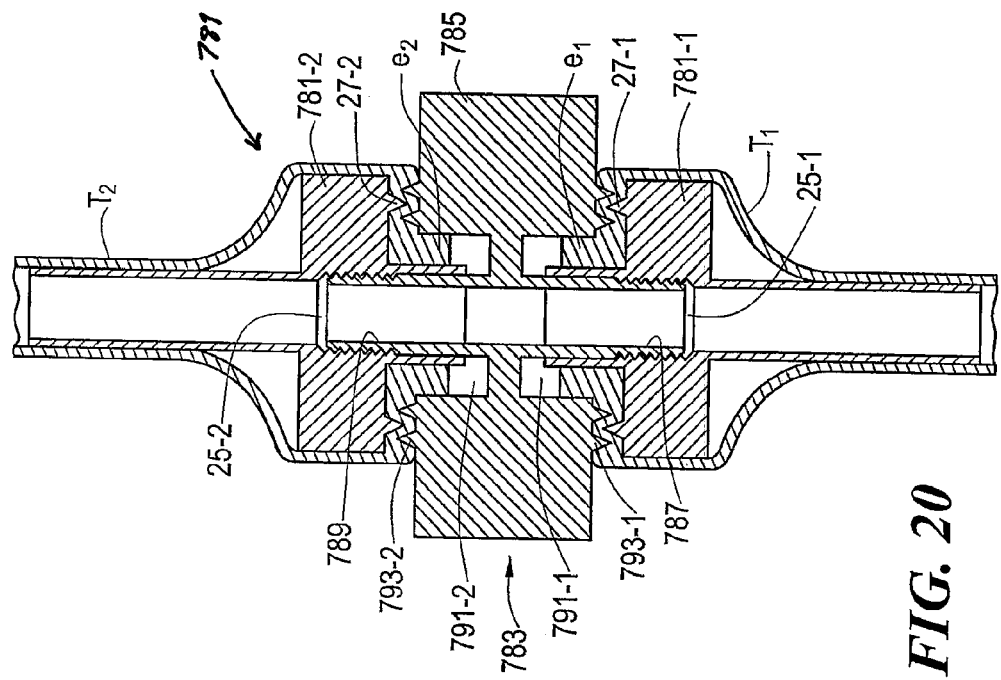
FIG. 20 is a section view of a pair of tubes interconnected using a first embodiment of a tube connecting assembly constructed according to the teachings of the present invention.

Referring now to FIG. 20, there are shown tubes $T_1$ and $T_2$ whose ends $e_1$ and $e_2$, respectively, are interconnected using a first embodiment of a tube connecting assembly constructed according to the teachings of the present invention, said tube connecting assembly being represented generally by reference numeral 781.

Assembly 781 comprises first and second connector portions 781-1 and 781-2, respectively, first and second connector portions 781-1 and 781-2 being identical to one another and to lower connector portion 13 of adaptor 11. As can be seen in FIG. 20, when interconnecting tubes $T_1$ and $T_2$, end $e_1$ of tube $T_1$ is inserted over first connector portion 781-1 and end $e_2$ of tube $T_2$ is inserted over second connector portion 781-2.

Assembly 781 further comprises a third connector portion 783. Third connector portion 783, which is a unitary structure preferably made of molded medical grade plastic, comprises a generally annular base 785 formed around a tubular member having an externally threaded bottom end 787 adapted to be screwed into bore 25-1 of first connector portion 781-1 and an externally threaded top end 789 adapted to be screwed into bore 25-2 of second connector portion 781-2. A first annular cavity 791-1 surrounds the tubular member and extends upwardly from the bottom of base 785, cavity 791-1 being adapted to receive end $e_1$ of tube $t_1$. A second annular cavity 791-2 surrounds the tubular member and extends downwardly from the top of base 785, cavity 791-2 being adapted to receive end $e_2$ of tube $t_2$. A first double walled lip 793-1 is formed on the bottom surface of base 785, and a second double walled lip 793-2 is formed on the top surface of base 785. Lips 793-1 and 793-2 are identical to lip 93 of adaptor 11, lip 793-1 being adapted to receive lip 27-1 of first connector portion 781-1 and lip 793-2 being adapted to receive lip 27-2 of second connector portion 781-2.

Figure 22:
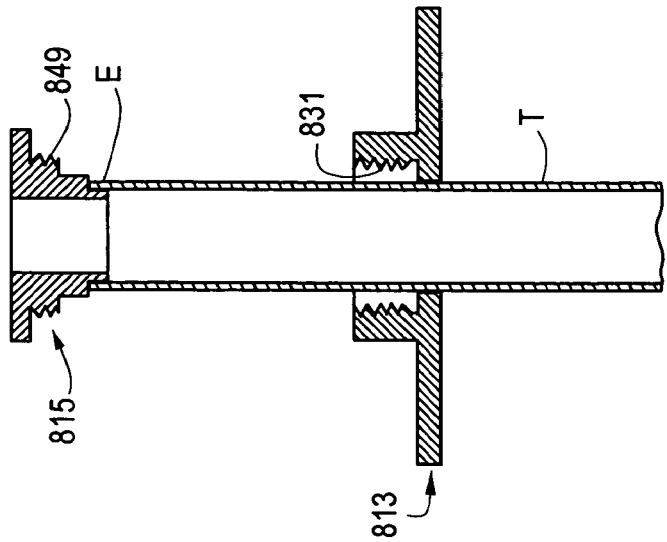
FIG. 22 is a section view of the adaptor of FIG. 21, with the upper and lower portions of the adaptor shown in an unassembled state and with the upper portion of the adaptor inserted into the proximal end of a gastrostomy feeding tube.
Figure 21:
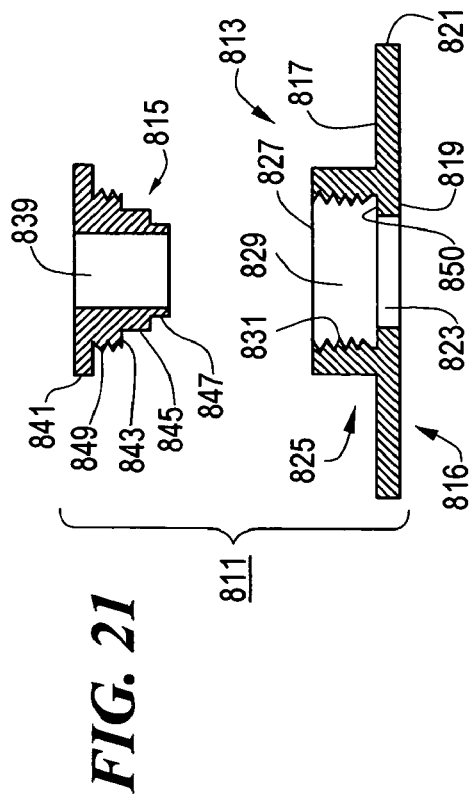
FIG. 21 is an exploded section view of a tenth embodiment of a low profile adaptor constructed according to the teachings of the present invention for use with a gastrostomy feeding tube.
Figure 23:
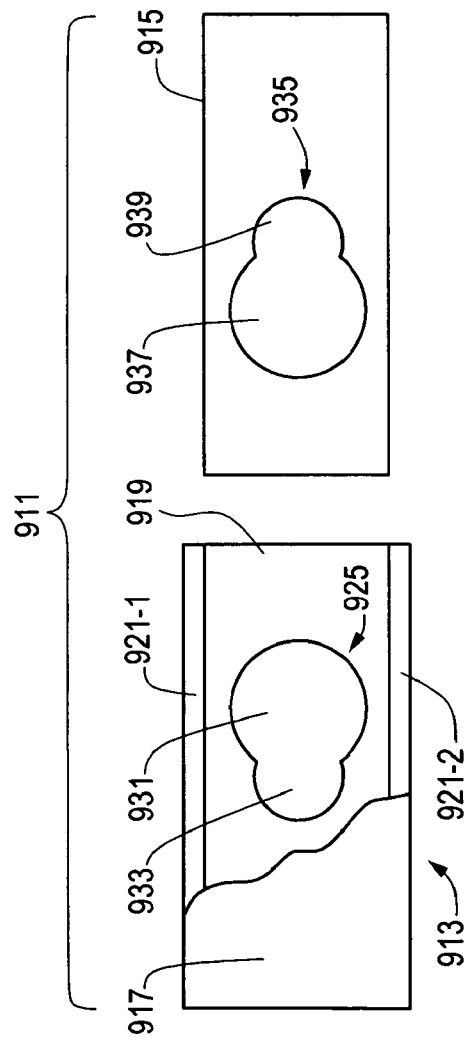
FIG. 23 is an exploded top view of one embodiment of an assembly constructed according to the teachings of the present invention for securing a barb-type fitting to a medical catheter.

Referring now to FIGS. 21 and 22, there is shown a tenth embodiment of a low profile adaptor constructed according to the teachings of the present invention, said low profile adaptor being shown attached to the proximal end E of a gastrostomy feeding tube T and being represented generally by reference numeral 811.

Adaptor 811 comprises a lower connector portion 813 and an upper connector portion 815.

Lower connector portion 813, which is a unitary structure preferably made of molded medical grade plastic, comprises an annular base section 816 having a top surface 817, a bottom surface 819, an outer surface 821 and a central bore 823. Bore 823 is appropriately dimensioned to permit a tube T to pass therethrough. Lower connector portion 813 further comprises a tubular member 825 extending upwardly from top surface 817, tubular member 825 being concentrically positioned around bore 823. Member 825 has an open top end 827 and a bore 829. A helical thread 831 is formed on the inside surface of member 825.

Upper connector portion 815, which is a unitary structure preferably made of molded medical grade plastic, is a generally annular member shaped to include a longitudinal bore 839 and a plurality of steps 841, 843, 845 and 847 of decreasing diameter from top to bottom. Step 841 is sized to rest upon top end 827 of tubular member 825 when upper connector portion 815 and lower connector portion 813 are assembled. A helical thread 849 is formed on the outside surface of step 843 for matingly engaging thread 831 when upper connector portion 815 and lower connector portions 813 are assembled. Step 845 is sized to rest upon bottom end 850 of tubular member 825 when upper connector portion 815 and lower connector portion 813 are assembled. Step 847 is sized for insertion into the proximal end E of a tube T.

In use, the proximal end E of a tube T is inserted up through bores 823 and 829. Step 847 is then inserted down into the proximal end of tube T. Upper connector portion 815 is then screwed down into lower connector portion 813 by matingly engaging threads 849 and 831.

Adaptor 811 is not limited to low profile use nor is it limited to use with gastrostomy feeding tubes.

Referring now to FIGS. 23 through 27, there are shown various views of an assembly for restricting the diameter of a medical catheter, for example, to tighten said catheter around a barb fitting or the like inserted thereinto, the assembly being constructed according to the teachings of the present invention and being identified generally by reference numeral 911.

Assembly 911 comprises a housing 913 and a slide 915, slide 915 being slidably mounted within housing 913.

Housing 913, which is a unitary structure preferably made of molded medical grade plastic, is a generally rectangular, hollow member having a top wall 917, a bottom wall 919, a pair of side walls 921-1 and 921-2, and a pair of open ends. A first opening 923 is formed on top wall 917, and a second opening 925, which is identical to first opening 923 and aligned therewith, is formed on bottom wall 919. Each of first opening 923 and second opening 925 comprises a first area 931 of comparatively greater diameter and a second area 933 of comparatively lesser diameter. For reasons to become apparent below, area 931 has a diameter greater than that of the medical catheter with which assembly 911 is intended to be used whereas area 933 has a diameter smaller than that of the medical catheter.

Slide 915, which is a unitary structure preferably made of molded medical grade plastic, is a generally rectangular plate. An opening 935 comprising a first area 937 of comparatively greater diameter and a second area 939 of comparatively lesser diameter is provided in slide 915, opening 935 being a mirror image of openings 923 and 925.

In use, slide 915 is first positioned within housing 913 so that area 937 of opening 935 is aligned with area 931 of openings 923 and 925. As can be seen in FIGS. 24 and 25, this positioning results in the formation of a transverse hole having the diameter of area 931. With assembly 911 thus positioned, the proximal end of a medical catheter is then inserted up through openings 925, 935 and 923, respectively. A barb-type fitting is then inserted into the proximal end of the medical catheter. Assembly 911 is then moved proximally until the distal end of the barb-type fitting and the proximal end of the medical catheter are positioned within openings 925, 935 and 923. Slide 915 is then moved so that area 939 of opening 935 is aligned with area 933 of openings 923 and 925. As can be seen in FIGS. 26 and 27, this results in the formation of a transverse hole having the diameter of area 933, causing assembly 911 to pinch the end of the catheter against the barb-type fitting.

An alternative slide 971 adapted for use with housing 913 is shown in FIG. 28. Slide 971 differs from slide 915 in that slide 971 has an opening 973 in which there is a smoother transition from larger area 975 to smaller area 977 than is the case with opening 935 of slide 915. (This smoother transition can also be applied to the shape of openings 923 and 925 in housing 913.) Slide 971 also differs from slide 915 in that slide 971 additionally includes an arcuate wall 981 that extends from the top and bottom surfaces of slide 971 so that, when assembly 911 is in its closed position, slide 971 engages the tube at the same level that housing 913 does.

As can readily be appreciated, housing 913 could be modified to eliminate one or more of walls 917, 921-1 and 921-2.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An adaptor for use with a medical catheter, said adaptor comprising:
    a first connector portion, the first connector portion comprising a first annular portion and a first tubular portion extending along a longitudinal axis, wherein the first annular portion has a proximal end and a distal end, and is adapted to be received within the medical catheter; and
    a second connector portion comprising a second tubular portion extending along a longitudinal axis, said second tubular portion having a cylindrical wall defining a longitudinal lumen therein, and said second connector portion further comprising a second annular portion having a proximal end, a distal end, an inner annular wall, an outer annular wall, and an annular cavity defined between the cylindrical wall and the inner annular wall for receiving the first end of a medical catheter therein,
    wherein a proximal end of the first connector portion and a distal end of the second connector portion are adapted to engage each other to hold the medical catheter therebetween,
    wherein the first tubular portion extends proximally beyond the proximal end of the first annular portion, and the second tubular portion extends distally beyond the distal end of the second annular portion.

2. The adaptor of claim 1, said first annular portion having a top surface extending perpendicular to the longitudinal axis, and said second annular portion having a bottom surface extending perpendicular to the longitudinal axis, wherein the top surface of the first annular portion and the bottom surface of the second annular portion are configured to receive the medical catheter therebetween.

3. The adaptor of claim 2, wherein the first connector portion and the second connector portion are adapted to apply pressure to the medical catheter in a direction parallel to the longitudinal axis.

4. The adaptor of claim 1, wherein the first tubular portion is configured to engage the second tubular portion.

5. The adaptor of claim 1, wherein said second annular portion includes a second cavity in fluid communication with said second tubular portion.

6. The adaptor of claim 5, further comprising a gasket-type valve seated in said second cavity.

7. The combination of
    a medical catheter having a bore; and
    the adaptor as claimed in claim 1, wherein the first connector portion is inserted into the bore of the medical catheter.

8. An adaptor for use with a medical catheter, said adaptor comprising:
    a first connector portion, the first connector portion comprising a first annular portion and a first tubular portion extending along a longitudinal axis, wherein the first annular portion is adapted to be received within the medical catheter; and
    a second connector portion comprising a second tubular portion extending along a longitudinal axis, said second tubular portion having a cylindrical wall defining a longitudinal lumen therein, and said second connector portion further comprising a second annular portion having an inner annular wall, an outer annular wall, and an annular cavity defined between the cylindrical wall and the inner annular wall for receiving the first end of a medical catheter therein,
    wherein the first connector portion and the second connector portion are adapted to engage each other to hold the medical catheter therebetween,
    said first annular portion having a top surface extending perpendicular to the longitudinal axis, and said second annular portion having a bottom surface extending perpendicular to the longitudinal axis, wherein the top surface of the first annular portion and the bottom surface of the second annular portion are configured to receive the medical catheter therebetween,
    wherein the top surface of the first annular portion and the bottom surface of the second annular portion have complementary means for engaging the medical catheter therebetween.

9. The adaptor of claim 8, wherein the complementary means is selected from the group consisting of:
    a circular lip formed on said first connector portion and a complementary groove formed in said second connector portion;
    an annular step formed on said first connector portion and a complementary cavity formed in said second connector portion;
    an annular sleeve formed on said second connector portion and a complementary groove formed on said first connector portion; and
    an annular flange formed on said first connector portion and a complementary cavity formed in said second connector portion.

10. An assembly for restricting the diameter of a medical catheter comprising:
    a planar housing having a top wall, a bottom wall, and a housing opening,
    wherein the housing opening has a first housing opening area and a second housing opening area,
    wherein the first housing opening area is larger than the second housing opening area; and
    a planar slide adapted to be slidably positioned in the housing, said planar slide having a slide opening therethrough,
    wherein the slide opening has a first slide opening area and a second slide opening area, wherein the first slide opening area is larger than the second slide opening area,
    wherein positioning the planar slide relative to the planar housing adjusts the alignment of the first housing opening area and the second housing opening area relative to the first slide opening area and the second slide opening area, and
    wherein the assembly has a first position in which the first housing opening area is aligned with the first slide opening area, and a second position in which the second housing opening area is aligned with the second slide opening area.

11. The assembly of claim 10, wherein the first housing opening area has a diameter that is greater than the diameter of the medical catheter to be received therethrough.

12. The assembly of claim 10, wherein the second housing opening area has a diameter that is less than the diameter of the medical catheter to be received therethrough.

13. The assembly of claim 10, wherein the first slide opening area has a diameter that is greater than the diameter of the medical catheter to be received therethrough.

14. The assembly of claim 10, wherein the second slide opening area has a diameter that is less than the diameter of the medical catheter to be received therethrough.

15. The assembly of claim 10, wherein the medical catheter is adapted to be inserted into the assembly when the assembly is in the first position.

16. The assembly of claim 10, wherein the medical catheter is adapted to be pinched in the assembly when the assembly is in the second position.

* * * * *